United States Patent [19]
Glenville

[11] Patent Number: 5,606,126
[45] Date of Patent: Feb. 25, 1997

[54] APPARATUS AND A METHOD FOR AUTOMATICALLY MEASURING THE DENSITY OF AN OBJECT

[75] Inventor: Reginald P. Glenville, Preston, United Kingdom

[73] Assignee: British Nuclear Fuels PLC, Warrington, United Kingdom

[21] Appl. No.: 202,116

[22] Filed: Feb. 25, 1994

[30] Foreign Application Priority Data

Feb. 26, 1993 [GB] United Kingdom ............. 9303887

[51] Int. Cl.⁶ .................................................. G01N 9/10
[52] U.S. Cl. ...................... 73/433; 73/437; 318/568.1; 177/148
[58] Field of Search ............... 73/433, 435, 437, 73/32 R; 177/148; 318/568.1; 901/9, 12, 18; 395/94, 95, 96

[56] References Cited

U.S. PATENT DOCUMENTS

| | | | |
|---|---|---|---|
| 3,747,416 | 7/1973 | Wommack | 73/437 |
| 3,787,761 | 1/1974 | Grossman et al. | 73/433 |
| 3,991,619 | 11/1976 | Appleford et al. | 73/437 |
| 4,320,658 | 3/1982 | Hilton et al. | 73/437 |
| 4,588,349 | 5/1986 | Rewter | 414/786 |

FOREIGN PATENT DOCUMENTS

| | | | |
|---|---|---|---|
| 2513758 | 4/1983 | France | 73/433 |
| 0210543 | 12/1983 | Japan | 73/433 |
| 1095128 | 12/1967 | United Kingdom | 73/433 |

*Primary Examiner*—Hezron E. Williams
*Assistant Examiner*—Helen C. Kwok
*Attorney, Agent, or Firm*—Nixon & Vanderhye

[57] ABSTRACT

Apparatus for automatically measuring the density an object which comprises a first weighing device for weighing the object in a first medium which is dry, a second weighing device for weighing an object in a second medium which is wet and a robotic device having a first gripper to grip the object when dry and a second gripper to grip the object when wet the device being capable of controlling the first gripper so as to place the object on and remove it from the first weighing device and for controlling the second gripper so as to place the object on and remove it from the second weighing device.

19 Claims, 1 Drawing Sheet

APPARATUS AND A METHOD FOR AUTOMATICALLY MEASURING THE DENSITY OF AN OBJECT

BACKGROUND OF THE INVENTION

1. Field of the Invention

The present invention relates to an apparatus and a method for automatically measuring the density of an object.

2. Discussion of Prior Art

In certain industries an important parameter to measure for quality assurance is the density of the product at an intermediate or final production stage. For example, in the production of nuclear fuel pellets made from sintered $UO_2$ it is necessary to ensure that the density of the pellets is within a narrow specified range to ensure that the pellets are suitable for their application.

In a known system for automatically measuring the density of objects such as nuclear fuel pellets it is known to measure the density by measuring the weight and the volume and by dividing one by the other. The volume is measured indirectly by measuring the dimensions of the objects and applying a geometrical formula to calculate the volume. Errors can occur if defects such as chips exist on the surface of the object.

SUMMARY OF THE INVENTION

According to the present invention in a first aspect there is provided apparatus for automatically measuring the density of an object which comprises a first weighing means for weighing the object in a first medium which is dry, a second weighing means for weighing an object in a second medium which is wet and a robotic device having a first gripper means to grip the object when dry and a second gripper means to grip the object when wet the device being capable of controlling the first gripper means so as to place the object on and remove it from the first weighing means and for controlling the second gripper means so as to place the object on and remove it from the second weighing means.

Desirably, the apparatus also includes a stage on which an object can be placed temporarily in the dry medium whereby the object may be transferred from the first gripper means after weighing by the first weighing means to the second gripper means prior to being immersed and weighed in the wet second medium.

The first medium may conveniently be air and the second medium may conveniently be water of known density, eg distilled water containing a known concentration of wetting agent at a known temperature. Desirably, the apparatus includes means for measuring the temperature of the second medium. The temperature of the first medium may be measured also if required.

According to the present invention in a second aspect there is provided a method for automatically measuring the density of an object using the apparatus of the first aspect which comprises the steps of: (a) placing the object by the first gripper means on the first weighing means; (b) weighing the object on the first weighing means; (c) removing the object from the first weighing means by the first gripper means; (d) transferring the object from the first gripper means to the second gripper means; (e) placing the object by the second gripper means on the second weighing means; (f) weighing the object on the second weighing means; and (g) removing the object from the second weighing means by the second gripper means.

Desirably, the object after step (g) is dried eg by transferring the object by the second gripper means to a region where the air from an air drier may be applied.

By using in the apparatus and method according to the present invention different gripper means to handle the object when weight measurements in the first and second media respectively are required, it is ensured that the first gripper means and first weighing means remain dry, ie are not wet by the liquid of the second medium. The first weighing means is thereby able to make repeated measurements without error caused by unwanted wetting.

The first and second gripper means may each comprise two or more fingers which can grip the object by a known pneumatic mechanism.

When the object is, for example, weighed in air as the first medium and then submerged and weighed in water as the second medium it will experience (according to Archimedes' Principle) an upthrust equal to the weight of the volume of water displaced. The density D of the object is calculated from the formula:

$$D = \frac{W1 \times d}{W1 - W2}$$

where W1 is the weight of the object in air, W2 is the weight of the object in water and d is the density of the water.

The first and second weighing means each desirably comprises a weighing pan and an analytical balance capable of providing an electrical output signal related to the applied load. The two weighing pans may be connected so that the weights recorded by the two weighing pans may be recorded by a common balance which may, for example, be a known balance operating on the principle of electromagnetic force compensation. The output signals from the balance may be applied to a signal processor which is capable of calculating the density D from signals representing W1 and W2 according to the formula given above. An input to the processor representing the water density d will be applied as a predetermined factor (which varies with temperature).

Desirably, the balance includes a facility for so-called "FACT" (fully automatic calibration). The balance may have means for calibrating the balance, when triggered by an operator, by internally loading reference weights, eg in a motorised operation, so that the processor may calculate a calibration factor which is stored until the next calibration. The means for calibration may itself be checked from time-to-time by using the apparatus and method to measure the density of an object of very accurately known density.

Desirably, the apparatus includes means for applying, as inputs to the processor, suitable correction signals which apply corrections known to be required. Examples of such corrections are given hereinafter.

The present invention may advantageously be used for the automatic measurement of the density of nuclear fuel pellets, eg unground uranium dioxide pellets. The pellets may be taken as samples from a production line of pellets being conveyed in a automatic fuel pellet production plant. After measurement and drying by the apparatus according to the present invention the pellets may be replaced in the production line.

Measurement of fuel pellet density automatically by the present invention allows the hazards associated with human handling of radioactive materials to be avoided.

Furthermore, the method according to the present invention is superior to the aforementioned prior art method in that measurement errors caused by surface defects such as chips are avoided because the method according to the present invention is essentially not dependent upon object shape or dimensions.

Desirably, when the objects are lowered by the second gripper means of the robotic device in the apparatus and method according to the present invention into the second medium to be weighed therein, the objects are lowered carefully so that air bubbles caused by movement in the second medium are avoided.

BRIEF DESCRIPTION OF THE DRAWINGS

Embodiments of the present invention will now be described by way of example with reference to the accompanying drawings, in which.

DETAILED DESCRIPTION OF PREFERRED EMBODIMENTS

Figure 1:
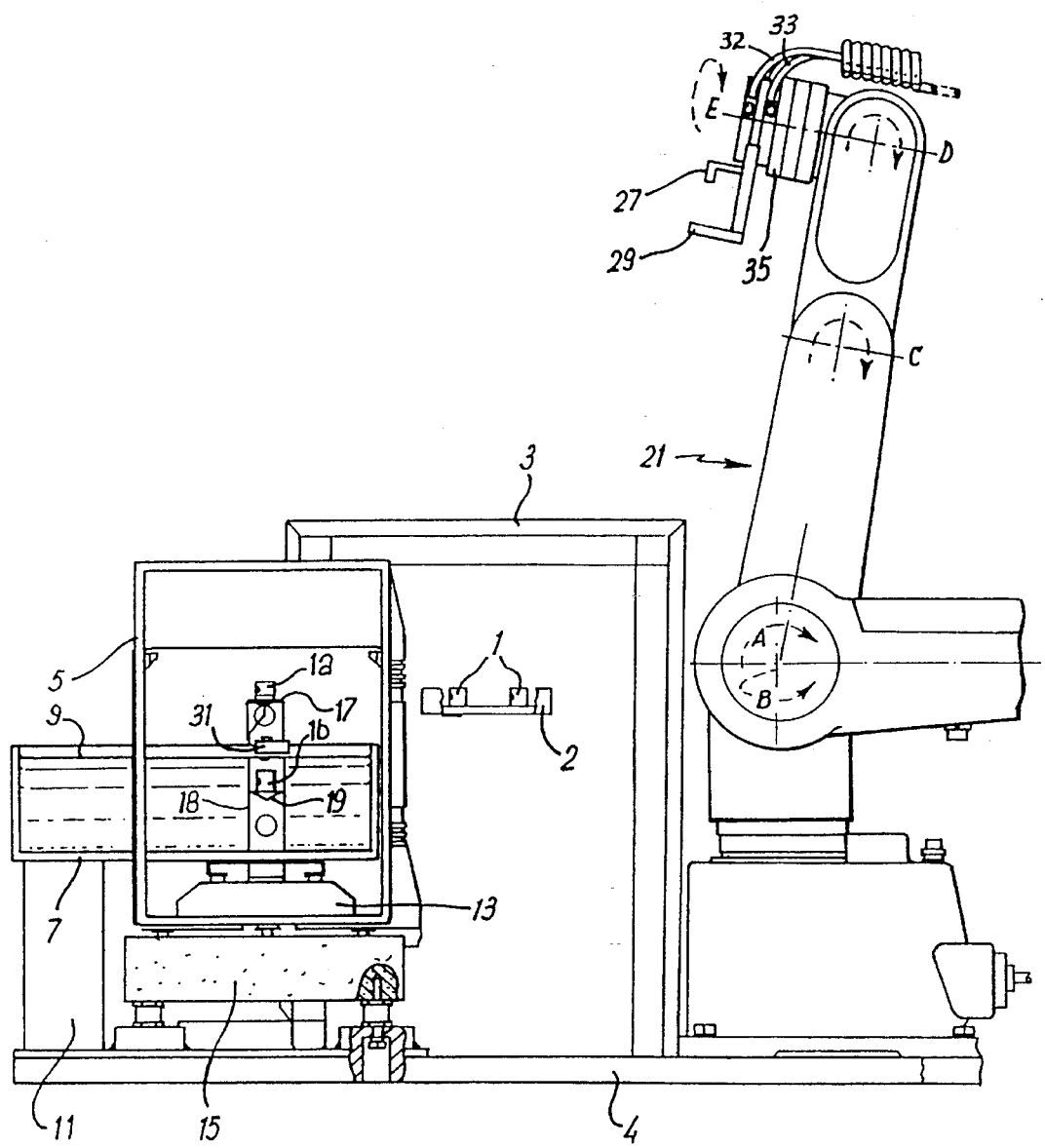
FIG. 1 is a partly cross-sectional side elevation of apparatus for automatically measuring the density of nuclear fuel pellets.

Referring to FIG. 1, the pellets to be weighed are sintered $UO_2$ pellets 1 travelling along a pellet conveyer 2 in a direction perpendicular to the plane of the drawing. The conveyer 2 runs inside an enclosure 3 which has a top opening in the region of the present autodensity measurement apparatus which apparatus is provided on the top surface of a table 4. Measurements of the weight of the pellets 1 are taken inside a container 5 in which is provided a tank 7 of distilled water having a surface level 9. The tank 7 is supported outside the container 5 by a column 11 on the table 4 and inside the container 5 by an accurately adjustable support 13 on the base of the container 5.

The container 5 is itself on an accurately adjustable granite support base 15. A dry weighing pan 17 is provided inside the container 5. The pan 17 is connected via a metal strip 18 to a balance (not shown) whereby as a weight is applied to the pan 17 the strip 18 registers a force at the balance. A wet weighing pan 19 is suspended from the dry weighing pan 17. The pan 19 is submerged in the water in the tank 7 whereby when a pellet 1 is placed on the pan 18 the strip 18 again registers a force at the balance.

A robotic pick and place device 21 is located adjacent to the container 5. The device 21 has joints at positions A, B, C, D and E which gives the possibility of independent rotation about 5 separate axes as indicated by dashed lines. The joints are operated electro-mechanically. The device 21 also has two pairs of fingers 27 and 29 (one of each pair shown) which are operated pneumatically by air applied via air tubes 32, 33 and a parallel opening chuck 35. Both pairs of fingers 27, 29 may be attached to a single chuck 35 whereby the pairs of fingers open and close together.

In use, the fingers 27 are maintained dry and only the fingers 29 are allowed to become wet. The balance is tared before start of the measuring cycle. Pellets 1 whose density is to be measured are picked from the conveyer 3 by the fingers 27 and placed via an opening (not shown) in the wall of the container 5 on the dry weighing pan 17 where the weight of the pellet 1 in air is recorded by the balance. The pellet 1 in this position is denoted by the symbol 1a in FIG. 1.

After this dry weight measurement has been made, the pellet is picked up by the fingers 27 and deposited on a plate 31 attached to the outside wall of the container. The plate 31 acts as a pellet intermediate stage. From the plate 31, the pellet 1 is picked up by the fingers 29 and thereby lowered into the water in the tank 7 and placed on the wet weighing pan 19 where the weight of the pellet 1 under water is recorded. The pellet 1 in this position is denoted by the symbol 1b in FIG. 1.

After this wet weight measurement has been made, the pellet 1 is picked up by the fingers 29 and transferred to a drying station (not shown) where the pellet 1 and fingers 29 are dried by the application of air from an air drier. Finally, the pellet 1 is returned to the conveyer 2.

The output of the balance is applied to a processor (not shown) which calculates the density of the material of the pellet 1 in the manner described above using the aforementioned corrections. The temperature of the water inside the tank 7 is monitored and the output is fed to the processor so that any necessary corrections in the density calculation to account for temperature changes can be made and applied.

From time-to-time, eg after a given number of pellets, eg five, have been sampled, a reference or dummy pellet made of stainless steel of precisely known weight and density is made the subject of density measurement according to the procedure described above. The result obtained from this measurement ensures that the auto-calibration of the balance is within pre-defined limits and that the system is functioning properly. The measurement of the previously sampled number, eg five, pellets is considered to be correct only after the reference pellet measurement has been found to be acceptable. If the reference pellet measurement is found not to be acceptable the previously sampled pellets must be re-introduced into the series of pellets to be weighed and the functioning of the system must be further investigated.

In the apparatus according to the present invention as exemplified by the apparatus shown in FIG. 1 the following corrections may be applied during the sample density calculations:

(1) Corrections to the sample dry weight W1

(a) Water level correction

This first correction is necessary if it is found that the placing of the pellet 1 on the dry weighing pan 17 causes it to deflect and submerge more than a given level of the wet weighing pan 19 in the water in the tank 7. This correction K1 is applied in accordance with:

$$W1 = M + K1$$

where W1 is the true dry weight and M is the reading obtained as an output from the balance.

(b) Air buoyancy effect corrections

The density of the object is assumed to be a given arbitrary value eg 8 $gcm^{-1}$. If the object eg pellet 1 being weighed has a density less or greater than this a correction factor A1 needs to be calculated as follows:

$$A1 = 1 + \left[ \left( \frac{1}{D} - \frac{1}{D1} \right) \times Da \right]$$

where D is the density of the object being measured, D1 is the arbitrary assumed density and Da is the density of air which may be assumed to be 0.0012 $gcm^{-1}$ at normal room temperatures. The correction factor A1 is then applied in accordance with:

$$W1 = W1' \times A1$$

where W1' is the measured dry weight. A1 may be calculated as 0.999961 for a $UO_2$ pellet (assumed density 10.8 $gcm^{-1}$) and 0.999986 for a Monel stainless steel standard pellet (assumed density 8.8 $gcm^{-1}$)

2. Corrections to the dry weight
   (a) water level correction

This first correction is necessary because as the object, eg pellet, submerges the water level rises slightly and affects the taring of the balance. (Before each pellet measurement the balance can be re-zeroed. This eliminates errors due to the water level changing over a long period of time).

This correction K2 may be set to 0.002 g and is determined by experiment. It is applied in accordance with $$W2 = M + K2$$

where W2 is the true wet weight.

(b) air buoyancy correction

This second correction A2 is again to compensate for air buoyancy as in 1(b) and is constant for all material of a given type; it is calculated as follows:

$$A2 = 1 - \frac{Da}{D1}$$

The correction factor A2 is applied as follows:

$$W2 = W2' \times A12$$

where W2' is the measured wet weight.

For $UO_2$ A2 can be calculated as 0.99985

3. Density of water

The density of the water/wetting agent solution has been calculated for various temperatures in 0.5° C. steps. At the time of each wet weighing the water temperature is measured and the appropriate water density value is selected from a stored table.

4. Sample density

The density of the reference pellet which is measured after each set of sampled pellets is corrected to a 20° C. value if the water temperature is significantly different from 20° C. If the reference pellet is manufactured from Monel alloy it will have a relatively high coefficient of thermal expansion compared with $UO_2$. A similar correction could be applied to the measured $UO_2$ pellets as well but may not be considered necessary.

I claim:

1. Apparatus for automatically measuring the density of an object in a series of objects, said apparatus comprising:

a first weighing means for weighing the object in a first medium which is dry;

an intermediate stage for temporarily receiving said object after being weighed in said dry medium;

a second weighing means for weighing the object in a second medium which is wet, said first and second weighing means comprising respective first and second weighing pans connected to at least one analytical balance;

a robotic pick and place device having a first gripper means for gripping the object when dry and a second gripper means for gripping the object when wet, the device comprising control means for controlling the first gripper means to place the object on and remove the object from the first weighing means and place the object on said intermediate stage and for controlling the second gripper means to pickup said object from said intermediate stage and to place the object on and remove the object from the second weighing means, said at least one balance providing electrical output signals related to the weight of said object on said first and second weighing pans; and signal processing means, responsive to said electrical output signals, for calculating the density of said object.

2. Apparatus as in claim 1 wherein the first and second gripper means each comprise two or more fingers which can grip the object by a pneumatic mechanism.

3. Apparatus as in claim 1 wherein said weighing pans are connected and said at least one analytical balance comprises a common balance.

4. Apparatus as in claim 3 wherein said common balance operates on the principle of electromagnetic force compensation.

5. Apparatus as in claim 3 wherein said common balance includes a facility for fully automatic calibration.

6. A method for automatically measuring the density of an object using the apparatus as in claim 1 which comprises the steps of:

(a) placing the object by the first gripper means on the first weighing means;

(b) weighing the object on the first weighing means;

(c) removing the object from the first weighing means by the first gripper means;

(d) transferring the object from the first gripper means to the second gripper means at an intermediate stage location;

(e) placing the object by the second gripper means on the second weighing means;

(f) weighing the object on the second weighing means;

(g) removing the object from the second weighing means by the second gripper means; and (h) calculating the density of said object from the weight of said object obtained from said first and second weighing means.

7. A method as in claim 6 wherein the object, after step (g), is dried by transferring the object by the second gripper means to a region where the air from an air drier is applied.

8. A method as in claim 6 wherein said object is a nuclear fuel pellet.

9. A method of automatically measuring the density of an object in a series of objects conveyed along a conveying track which comprises the steps of:

(a) conveying the series of objects to an object density measuring station which includes:

(i) a density measuring apparatus comprising a first weighing support for weighing each said object in a first medium which is dry, the first weighing support connected to a weight recorder which records the weight of the object on the first weighing support and a second weighing support for weighing each said object in a second medium which is wet, the second weighing support connected to a weight recorder which records the weight of the object on the second weighing support; and (ii) a pick and place device which has a first gripper for picking up and holding said object and for releasing said object and a second gripper for picking up and holding said object and for releasing said object;

(b) picking up a selected specimen object from the series of objects by the first gripper and placing the specimen object on the first weighing support;

(c) weighing the specimen object on the first weighing support in the first medium;

(d) removing the specimen object from the first weighing support by the first gripper and placing the specimen object in an intermediate stage location to be picked up by the second gripper;

(e) picking up the specimen object by the second gripper and placing the specimen object on the second weighing support;

(f) weighing the specimen object on the second weighing support in the second medium;

(g) returning the specimen object to the series of objects; and (h) calculating, based upon weight of said object in said first medium and weight of said object in said second medium, the density of said object.

10. A method as in claim 9 wherein in step (d) the intermediate location is a dry stage on which said specimen object is placed by the first gripper and picked up from by the second gripper for placement on the second weighing support.

11. A method as in claim 9 wherein the first and the second grippers each comprise at least two fingers, which said fingers are actuated and grip the specimen object by a pneumatic mechanism.

12. A method as in claim 9 wherein each of the first and second weighing supports comprises a weighing pan and each said weighing pan is connected to an analytical weighing balance capable of providing an electrical output signal related to a load applied to the weighing pan.

13. A method as in claim 12 wherein each said weighing pan is connected to one another and the weights measured by weighing the specimen object in each said weighing pan are recorded by a common analytical weighing balance.

14. A method as in claim 13 wherein the weighing balance operates on the principle of electromagnetic force compensation.

15. A method as in claim 13 wherein the electrical output signal of the weighing balance is applied to a signal processor for calculating the density of the specimen object from signals representing dry and wet weights of the object.

16. A method as in claim 13 wherein the weighing balance includes a means for fully automatic self-calibration.

17. A method as in claim 9 wherein after step (f) the specimen object is dried by transferring the specimen object by the second gripper to a region where air from an air drier is applied to the surface of the specimen object.

18. A method as in claim 17 wherein the objects are nuclear fuel pellets.

19. A method as in claim 17 wherein included in the objects are nuclear fuel pellets and dummy pellets being of known density to facilitate auto-calibration of the weight recorder.

* * * * *

UNITED STATES PATENT AND TRADEMARK OFFICE
CERTIFICATE OF CORRECTION

PATENT NO.    : 5,606,126
DATED         : February 25, 1997
INVENTOR(S)   : GLENVILLE It is certified that error appears in the above-identified patent and that said letters patent is hereby corrected as shown below:

Column 3, line 40, delete "18" and insert --19--.

Column 5, line 22, delete "A12" and insert --A2--.

Signed and Sealed this

Sixteenth Day of September, 1997

Attest:

BRUCE LEHMAN

Attesting Officer

Commissioner of Patents and Trademarks